(12) United States Patent
Shafer et al.

(10) Patent No.: US 10,665,331 B2
(45) Date of Patent: May 26, 2020

(54) DEVICE-BASED PARTICIPANT MATCHING

(71) Applicant: Accenture Global Services Limited, Dublin (IE)

(72) Inventors: Ian C. Shafer, Tabernacle, NJ (US); Chad A. Aston, Sonoma, CA (US); Sara Chan, Wayne, PA (US)

(73) Assignee: Accenture Global Services Limited, Dublin (IE)

( * ) Notice: Subject to any disclaimer, the term of this patent is extended or adjusted under 35 U.S.C. 154(b) by 856 days.

(21) Appl. No.: 15/016,825

(22) Filed: Feb. 5, 2016

(65) Prior Publication Data

US 2017/0124292 A1    May 4, 2017

Related U.S. Application Data

(60) Provisional application No. 62/247,978, filed on Oct. 29, 2015.

(51) Int. Cl.
| | |
|---|---|
| *G16H 10/20* | (2018.01) |
| *G06Q 10/10* | (2012.01) |
| *G06Q 50/22* | (2018.01) |
| *G06Q 10/06* | (2012.01) |
| *G16H 50/30* | (2018.01) |

(52) U.S. Cl.
CPC ....... *G16H 10/20* (2018.01); *G06Q 10/06311* (2013.01); *G06Q 10/109* (2013.01); *G06Q 50/22* (2013.01); *G16H 50/30* (2018.01)

(58) Field of Classification Search
CPC .................................................. G16H 10/20
See application file for complete search history.

(56) References Cited

U.S. PATENT DOCUMENTS

| | | | | |
|---|---|---|---|---|
| 2002/0099570 A1* | 7/2002 | Knight | ................. | G06F 19/324 705/2 |
| 2002/0143577 A1* | 10/2002 | Shiffman | ............... | G06Q 10/04 705/2 |
| 2004/0162035 A1* | 8/2004 | Petersen | ............ | A61B 5/02055 455/90.1 |
| 2006/0224561 A1* | 10/2006 | Bestgen | ............ | G06F 17/30457 |

(Continued)

FOREIGN PATENT DOCUMENTS

| | | |
|---|---|---|
| WO | WO 02/37213 | 5/2002 |
| WO | WO 2011/127249 A1 | 10/2011 |

OTHER PUBLICATIONS

Extended European search report corresponding to EP 16195468.0, dated Feb. 13, 2017, 7 pages.

*Primary Examiner* — John A Pauls
(74) *Attorney, Agent, or Firm* — Harrity & Harrity, LLP

(57) ABSTRACT

A device may obtain first data regarding a set of events. The device may obtain second data regarding a user. The device may process the first data and the second data to identify one or more events, of the set of events, for participation by the user. The device may receive, via a user interface, a selection of a particular event of the one or more events. The device may receive, via the user interface, a set of prompts relating to participation in the particular event. The device may detect an interaction with the user interface associated with responding to the set of prompts. The device may provide information identifying the user based on the interaction with the user interface associated with responding to the set of prompts.

20 Claims, 12 Drawing Sheets

(56) References Cited

U.S. PATENT DOCUMENTS

| | | |
|---|---|---|
| 2010/0153949 A1* | 6/2010 | Vincent .............. G06F 9/45558 718/1 |
| 2010/0222646 A1 | 9/2010 | Rao et al. |
| 2010/0246785 A1* | 9/2010 | Wang ................ H04M 1/72583 379/88.23 |
| 2012/0084100 A1 | 4/2012 | Tilles et al. |
| 2012/0089418 A1 | 4/2012 | Kamath et al. |
| 2012/0158420 A1 | 6/2012 | Lacal |
| 2013/0268282 A1 | 10/2013 | Hugo et al. |
| 2013/0332191 A1 | 12/2013 | Hoffman et al. |
| 2014/0108030 A1 | 4/2014 | Tejeda-Monteagut |
| 2014/0108427 A1 | 4/2014 | Spiegel |
| 2015/0135095 A1 | 5/2015 | Donneau-Golencer et al. |
| 2015/0161336 A1* | 6/2015 | Kalathil ................ G06Q 50/24 705/3 |
| 2015/0356582 A1* | 12/2015 | Turner, Jr. ............. H04W 4/02 705/7.34 |

* cited by examiner

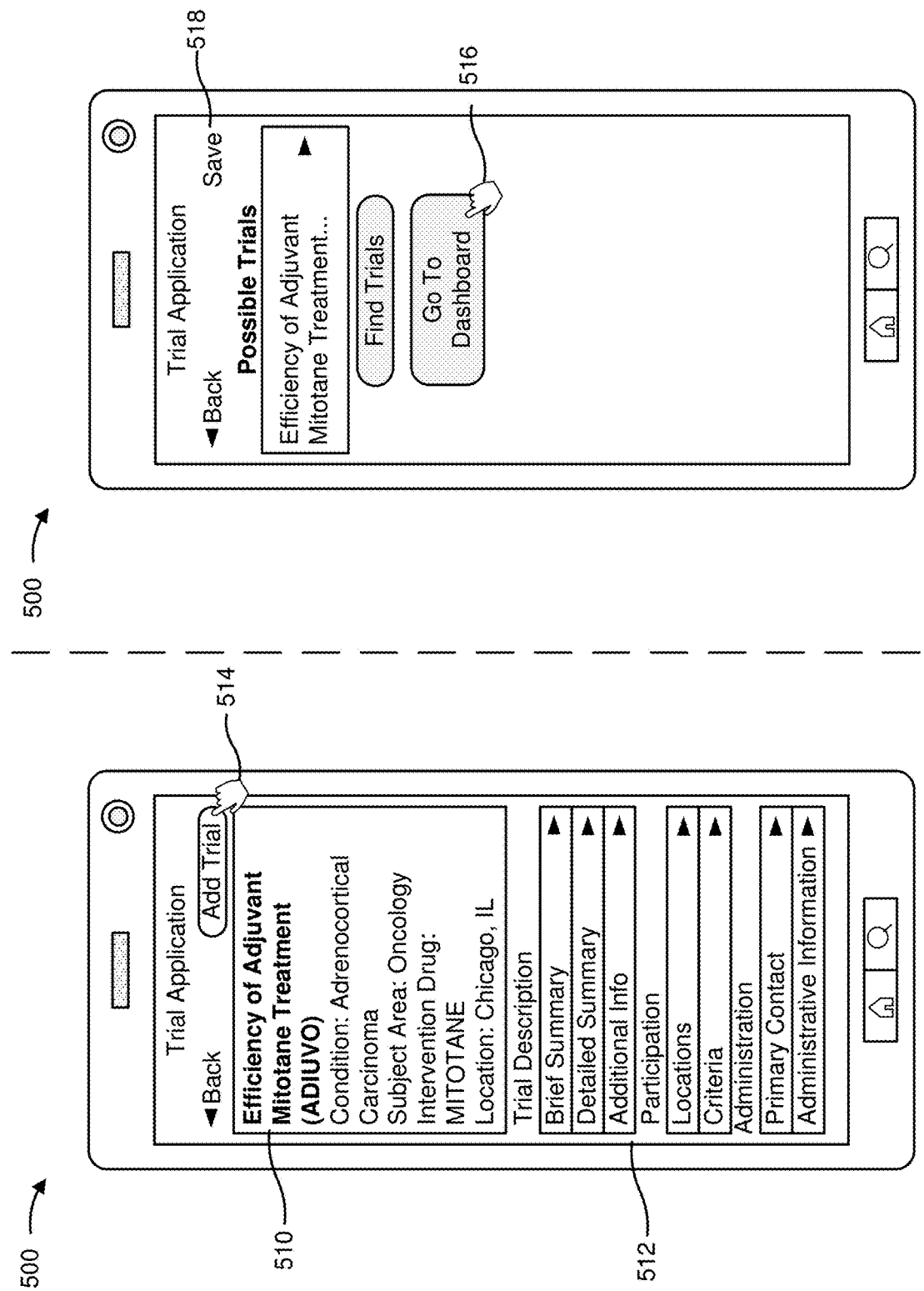

FIG. 5F

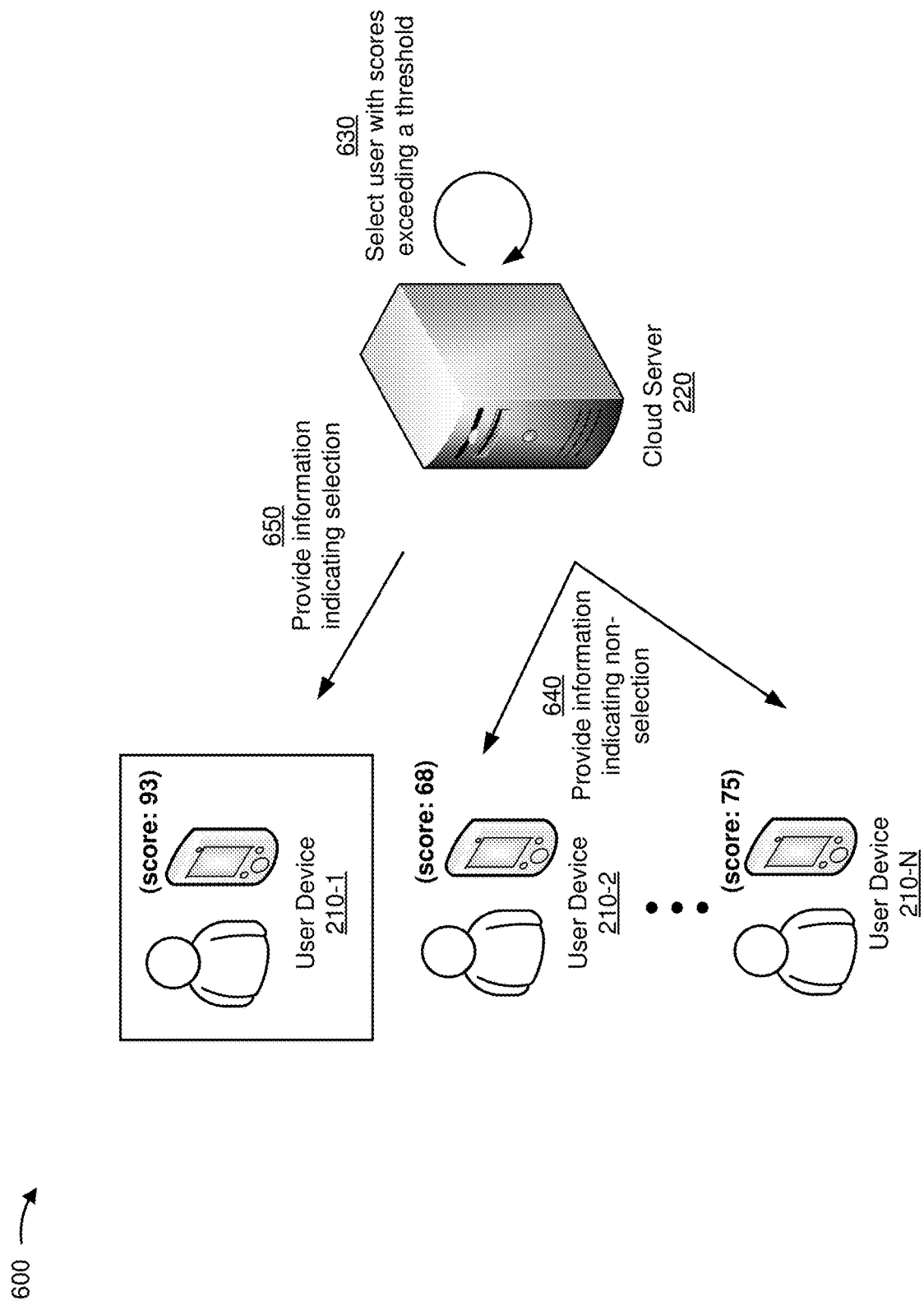

DEVICE-BASED PARTICIPANT MATCHING

RELATED APPLICATION(S)

This application claims priority under 35 U.S.C. § 119 to U.S. Provisional Patent Application No. 62/247,978, filed on Oct. 29, 2015, the content of which is incorporated by reference herein in its entirety.

BACKGROUND

A first party may desire to obtain information regarding a qualification of a second party for participation in an event. For example, an investigator may desire to obtain information regarding whether a group of potential patients are qualified for participation in a particular clinical trial. A patient, of the group of potential patients, may visit a doctor's office, and may receive information regarding treatments for a particular condition; however, the patient's doctor may not have information regarding the particular clinical trial for a number of reasons. For example, the patient's doctor may be unaffiliated with a hospital at which the particular clinical trial is being performed, may lack access to updated documents describing active clinical trials, may not be exposed to advertising regarding the particular clinical trial, or the like. As a result, patients may fail to receive information regarding clinical trials for which the patients are qualified and investigators may fail to receive sufficient patient interest to conduct the clinical trials.

SUMMARY

According to some possible implementations, a non-transitory computer-readable medium may store one or more instructions that, when executed by one or more processors, may cause the one or more processors to obtain, from a first device, first data regarding a set of events. The one or more instructions, when executed by one or more processors, may cause the one or more processors to obtain, from a second device, second data regarding a user. The one or more instructions, when executed by one or more processors, may cause the one or more processors to process the first data and the second data to identify one or more events, of the set of events, for participation by the user. The one or more instructions, when executed by one or more processors, may cause the one or more processors to receive, via a user interface, a selection of a particular event of the one or more events. The one or more instructions, when executed by one or more processors, may cause the one or more processors to provide, via the user interface, a set of prompts relating to participation in the particular event. The one or more instructions, when executed by one or more processors, may cause the one or more processors to detect an interaction with the user interface associated with responding to the set of prompts. The one or more instructions, when executed by one or more processors, may cause the one or more processors to provide information identifying the user based on the interaction with the user interface associated with responding to the set of prompts.

According to some possible implementations, a device may include one or more processors. The one or more processors may determine user information regarding a user. The user information may relate to one or more physical characteristics or mental characteristics of the user and a medical history of the user. The one or more processors may identify one or more clinical trials, of a set of potential clinical trials, for the user based on the user information. The one or more clinical trials may be associated with one or more attributes satisfied by the user based on the user information. The one or more processors may provide, for display via a first device associated with the user, information identifying the one or more clinical trials based on identifying the one or more clinical trials for the user. The one or more processors may provide, for display via a second device associated with an investigator of a particular clinical trial of the one or more clinical trials, information identifying the user.

According to some possible implementations, a method may include determining, by a device, user information regarding a user. The user may be a potential participant in a clinical trial. The user information may relate to one or more physical characteristics or mental characteristics of the user and/or a medical history of the user. The method may include determining, by the device, information associated with a set of clinical trials. The method may include matching, by the device, the user to a particular clinical trial, of the set of clinical trials, based on the user information and the information associated with the set of clinical trials. The method may include providing, by the device, information associated with the particular clinical trial for display via a user interface based on matching the user to the particular clinical trial.

BRIEF DESCRIPTION OF THE DRAWINGS

FIGS. 5A-5F are diagrams of an example implementation relating to the example process shown in FIG. 4; and FIGS. 6A-6C are diagrams of another example implementation relating to the example process shown in FIG. 4.

DETAILED DESCRIPTION

The following detailed description of example implementations refers to the accompanying drawings. The same reference numbers in different drawings may identify the same or similar elements.

A first party may be associated with a set of attributes that corresponds to the first party being qualified for an event. A second party may desire to identify one or more first parties associated with the set of attributes that corresponds to the one or more first parties being qualified for the event. For example, a potential participant (e.g., a first party) may be associated with a particular medical condition, a particular age, a particular gender, a particular family history, or the like that may qualify the potential participant to participate in a clinical trial. Similarly, an investigator (e.g., a second party) associated with the clinical trial may desire to identify potential participants in the clinical trial. The clinical trial may require a threshold quantity of participants, without which the clinical trial cannot be conducted.

The investigator may provide information regarding the clinical trial. For example, the investigator may hold meetings with doctors at the investigator's hospital, may advertise the clinical trial via media, or the like. However, a doctor of the potential participant may not be associated with the same hospital as the investigator and/or may not have been exposed to any advertisements regarding the clinical trial. Similarly, even if the potential participant is exposed to an advertisement regarding the clinical trial, the potential participant may lack the medical knowledge to understand that the potential participant is qualified for the clinical trial.

Implementations, described herein, may obtain information regarding qualifications for a set of clinical trials and may match the qualifications to attributes of a user (e.g., a potential participant) to match the user to a particular clinical trial of the set of clinical trials. In this way, a quantity of memory resources may be reduced based on providing clinical trial information for clinical trials for which potential participants are qualified relative to providing clinical trial information for all clinical trials regardless of whether a potential participant is qualified for a particular clinical trial. Similarly, a quantity of memory and processor resources may be reduced by providing a user with a list of clinical trials relative to a user manually searching for clinical trials through a variety of methods. Moreover, based on permitting patients to receive information regarding clinical trials, directly, a quantity of potential patients for a particular clinical trial may be increased (relative to relying on advertising and/or doctor notifications). In this way, users may be matched to clinical trials that can benefit the users and investigators can receive a sufficient quantity of participants to perform the clinical trials.

Figure 1A:
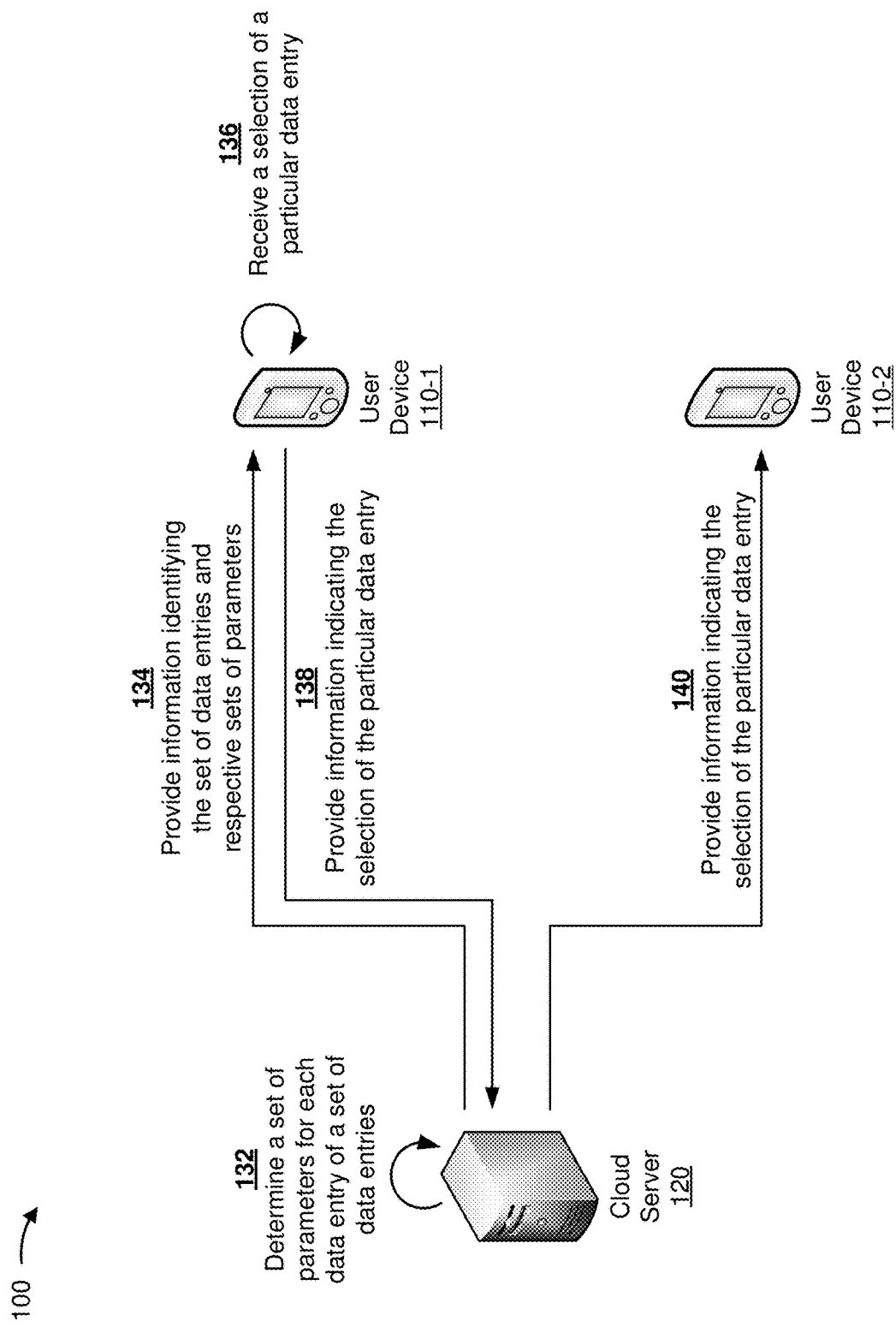
FIGS. 1A and 1B are diagrams of an overview of an example implementation described herein.
Figure 1B:
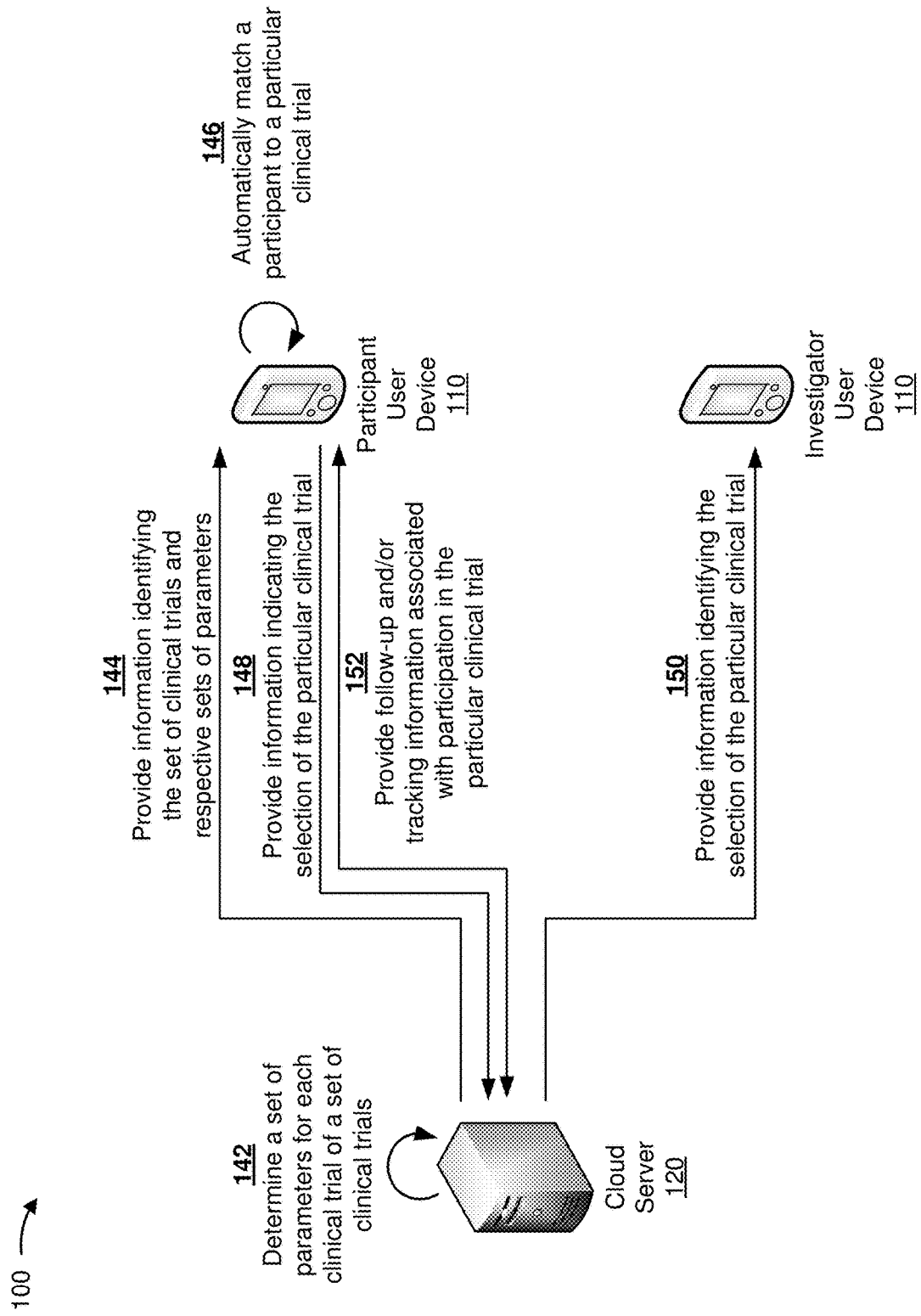

FIGS. 1A and 1B are diagrams of an overview of an example implementation 100 described herein. As shown in FIG. 1A, example implementation 100 may include a user device 110-1, a user device 110-2, and a cloud server 120. As shown by reference number 132, cloud server 120 may determine a set of parameters for each data entry of a set of data entries (e.g., a set of data entries identifying corresponding events). As shown by reference number 134, cloud server 120 may provide information identifying the set of data entries and respective sets of parameters. As shown by reference number 136, user device 110-1 may receive a selection of a particular data entry, of the set of data entries, based on a particular set of parameters, of the respective sets of parameters, associated with the particular data entry. Additionally, or alternatively, user device 110-1 may automatically select the particular data entry based on the particular set of parameters.

As shown by reference number 138, user device 110-1 may provide information indicating the selection of the particular data entry. Additionally, or alternatively, user device 110-1 may provide information identifying a set of attributes of a first party (e.g., a user of user device 110-1), and cloud server 120 may match the set of attributes of the first party to the particular data entry based on the particular set of parameters. Cloud server 120 may determine that the particular data entry is associated with a second party. Assume that the second party is associated with operating user device 110-2. As shown by reference number 140, cloud server 120 may provide information indicating the selection of the particular data entry to user device 110-2 for display to the second party. In this way, cloud server 120 may match a set of attributes of a first party to a data entry associated with a second party based on a set of parameters associated with the data entry.

As shown in FIG. 1B, example implementation 100 may include participant user device 110, investigator user device 110, and cloud server 120. As shown by reference number 142, cloud server 120 may determine a set of a parameters for each clinical trial of a set of clinical trials. For example, a user of investigator user device 110 (e.g., an investigator) may provide information identifying a particular clinical trial (e.g., via a user interface of investigator user device 110). The information identifying the particular clinical trial may include information identifying a medical condition, a gender, an age range, a family history, a location, or the like that may qualify a potential participant for the particular clinical trial. In some implementations, cloud server 120 may data mine a data structure. For example, cloud server 120 may parse a data structure storing information regarding clinical trials to determine respective sets of parameters for each clinical trial.

As further shown in FIG. 1B, and by reference number 144, cloud server 120 may provide information identifying the set of clinical trials and the respective sets of parameters associated with each clinical trial. As shown by reference number 146, participant user device 110 may automatically match a participant (e.g., a user of participant user device 110) to a particular clinical trial of the set of clinical trials. For example, participant user device 110 may obtain a set of attributes of the user, and may match the set of attributes to a particular set of parameters associated with the particular clinical trial. In some implementations, participant user device 110 may obtain the set of attributes based on providing a user interface to receive input, data mining information, or the like. Additionally, or alternatively, participant user device 110 may provide information identifying one or more matching clinical trials, and may receive a selection from the user via the user interface. As shown by reference number 148, cloud server 120 may receive information indicating the selection of the particular clinical trial. Additionally, or alternatively, cloud server 120 may receive information identifying the set of attributes associated with the user, and may automatically match the set of attributes to the particular set of parameters to match the user to the particular clinical trial. Additionally, or alternatively, cloud server 120 may periodically match groups of potential participants to one or more clinical trials, and may transmit notifications to the groups of potential participants.

As further shown in FIG. 1B, and by reference number 150, cloud server 120 may provide information identifying the selection of the particular clinical trial. For example, cloud server 120 may provide contact information for the user to investigator user device 110. Additionally, or alternatively, cloud server 120 may cause information identifying the user to be included in information regarding a set of potential participants. In some implementations, cloud server 120 may receive information indicating that the user is accepted into the clinical trial, and may provide the information to participant user device 110. Additionally, or alternatively, cloud server 120 may receive information indicating that the user is invited to attend an appointment for further screening prior to acceptance into the clinical trial. Additionally, or alternatively, cloud server 120 may provide and/or receive information associated with pre-screening the user for the clinical trial, and may schedule an appointment for the user to undergo further screening for the clinical trial. In some implementations, cloud server 120 may provide information regarding the clinical trial to one or more other potential participants. For example, cloud server 120 may identify one or more friends, family members, or the like of the user, and may contact the one or more friends, family members, or the like to solicit participation in the clinical trial.

As further shown in FIG. 1B, and by reference number 152, cloud server 120 and/or participant user device 110 may periodically transmit follow-up and/or tracking information regarding participation in the particular clinical trial. For example, cloud server 120 may receive instructions regarding a set of appointments to attend for the particular clinical trial, a set of screening meetings, a consent document, a contract, a waiver, or the like, and may provide information to participant user device 110 for display to the participant. Similarly, cloud server 120 may receive information, such as a confirmation that the participant intends to attend the set of screening meetings, a signed consent document, a signed waiver, or the like, and may provide the information to investigator user device 110.

In this way, cloud server 120 increases a likelihood that a user participates in a clinical trial, which may provide positive health outcomes to the user, relative to the user relying on recognizing advertising or receiving information from a doctor. Moreover, cloud server 120 increases a likelihood that a clinical trial receives a sufficient quantity of interest from potential participants to conduct the clinical trial relative to disseminating information regarding clinical trials person-to-person and/or via advertising. Furthermore, based on transmitting information regarding a clinical trial to a user device associated with a user interested and/or qualified for a particular clinical trial, cloud server 120 reduces a load on a communication network by reducing a quantity of messages transmitted relative to separately contacting each doctor of a group of doctors to disseminate information regarding the particular clinical trial to patients of the group of doctors (who may not qualify for the particular clinical trial).

As indicated above, FIGS. 1A-1B are provided merely as an example. Other examples are possible and may differ from what was described with regard to FIGS. 1A-1B.

Figure 2:
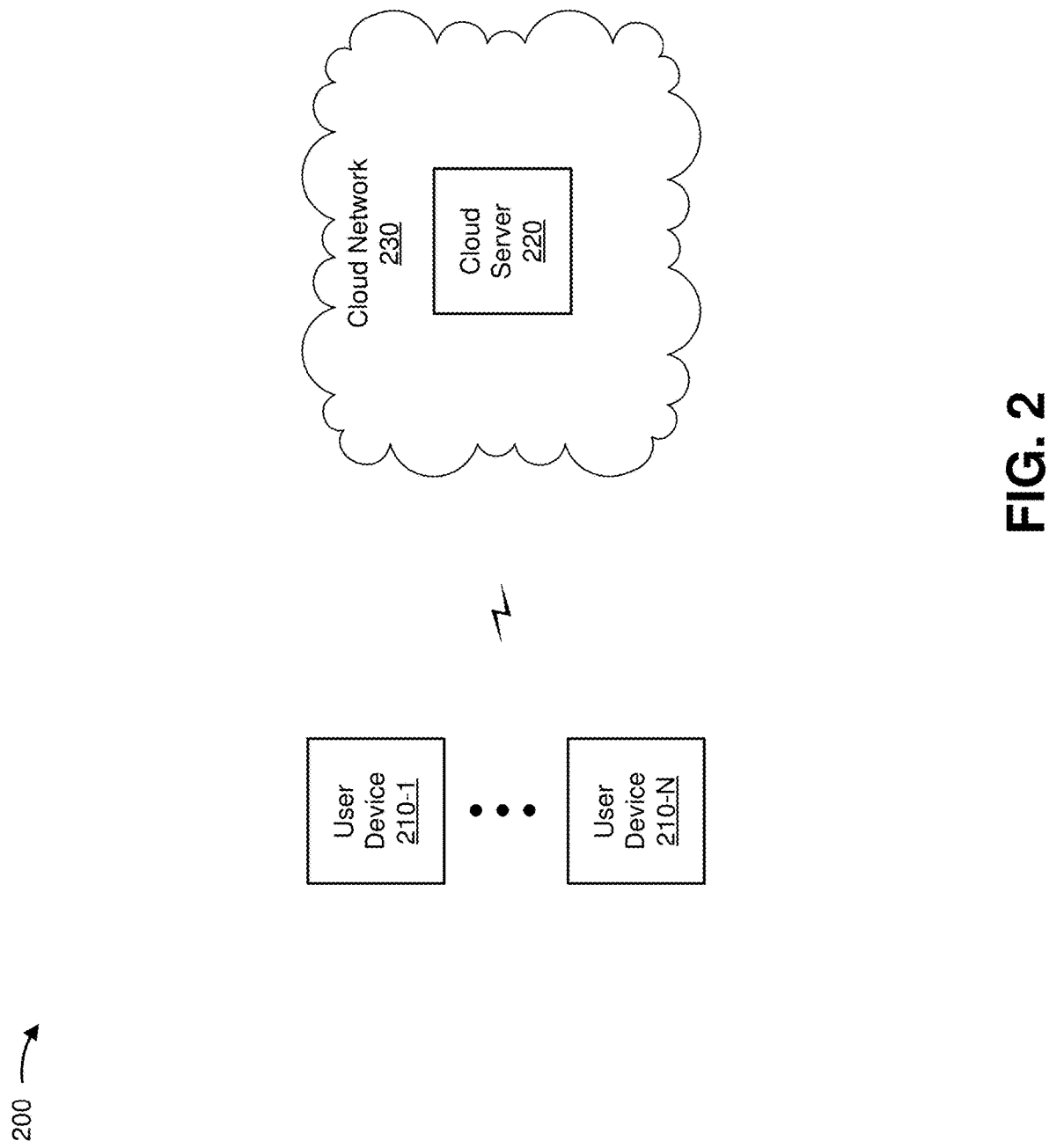
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include one or more user devices 210-1 through 210-N (N≥1) (hereinafter referred to collectively as "user devices 210," and individually as "user device 210"), a cloud server 220, and a cloud network 230. Devices of environment 200 may interconnect via wired connections, wireless connections, or a combination of wired and wireless connections.

User device 210 may include one or more devices capable of receiving, generating, storing, processing, and/or providing information associated with participation in an event (e.g., a clinical trial). For example, user device 210 may include a communication and/or computing device, such as a mobile phone (e.g., a smart phone, a radiotelephone, etc.), a computer (e.g., a laptop computer, a tablet computer, a handheld computer, a desktop computer, etc.), a wearable communication device (e.g., a smart wristwatch, a pair of smart eyeglasses, etc.), or a similar type of device. In some implementations, user device 210 may be utilized by an investigator associated with a clinical trial. In some implementations, user device 210 may be utilized by a potential participant in a clinical trial. In some implementations, user device 210 corresponds to user device 110-1, user device 110-2, participant user device 110, and/or investigator user device 110 shown in FIGS. 1A and 1B. In some implementations, user device 210 may receive information from and/or transmit information to another device in environment 200.

Cloud server 220 may include one or more devices capable of storing, processing, and/or routing information associated with participation in an event (e.g., a clinical trial). For example, cloud server 220 may include a server that is associated with matching participants to clinical trials. In some implementations, cloud server 220 corresponds to cloud server 120 shown in FIGS. 1A and 1B. In some implementations, cloud server 220 may include a communication interface that allows cloud server 220 to receive information from and/or transmit information to other devices in environment 200. While cloud server 220 is described as a resource in a cloud computing network, such as cloud network 230, cloud server 220 may operate external to a cloud computing network, in some implementations.

Cloud network 230 may include an environment that delivers computing as a service, whereby shared resources, services, etc. may be provided by cloud server 220 to store, process, and/or route information associated with matching participants to clinical trials. Cloud network 230 may provide computation, software, data access, storage, and/or other services that do not require end-user knowledge of a physical location and configuration of a system and/or a device that delivers the services (e.g., cloud server 220). As shown, cloud network 230 may include cloud server 220 and/or may communicate with user device 210 via one or more wired or wireless networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. For example, although user device 210 and cloud server 220 are shown as separate devices, user device 210 and cloud server 220 may be implemented in a single device. Additionally, or alternatively, a set of devices (e.g., one or more devices) of environment 200 may perform one or more functions described as being performed by another set of devices of environment 200.

Figure 3:
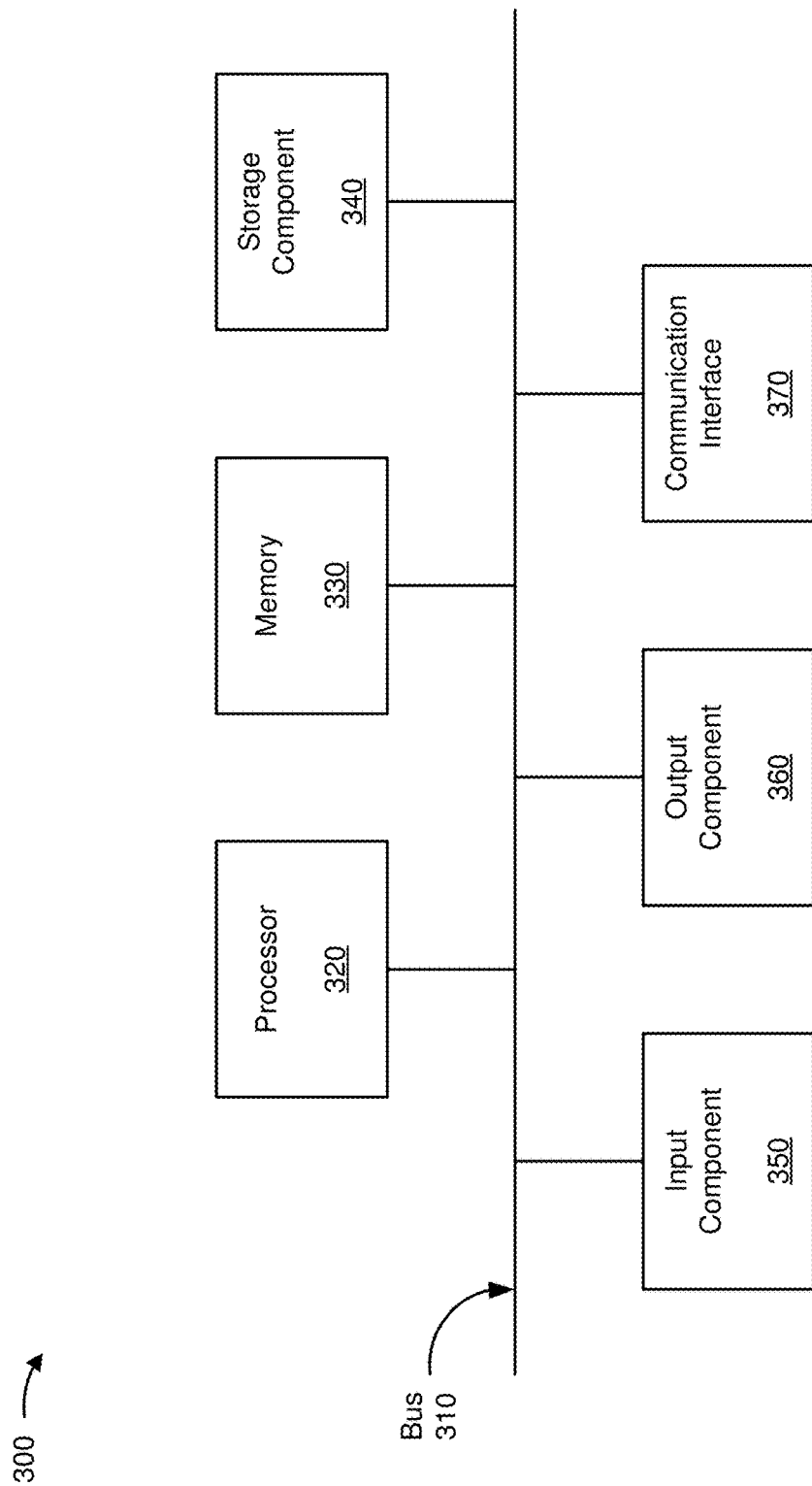
FIG. 3 is a diagram of example components of one or more devices of FIG. 2.

FIG. 3 is a diagram of example components of a device 300. Device 300 may correspond to user device 210 and/or cloud server 220. In some implementations, user device 210 and/or cloud server 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 is implemented in hardware, firmware, or a combination of hardware and software. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an h-specific integrated circuit (ASIC), etc.) that interprets and/or executes instructions. In some implementations, processor 320 may include one or more processors that can be programmed to perform a function. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 350 may include a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
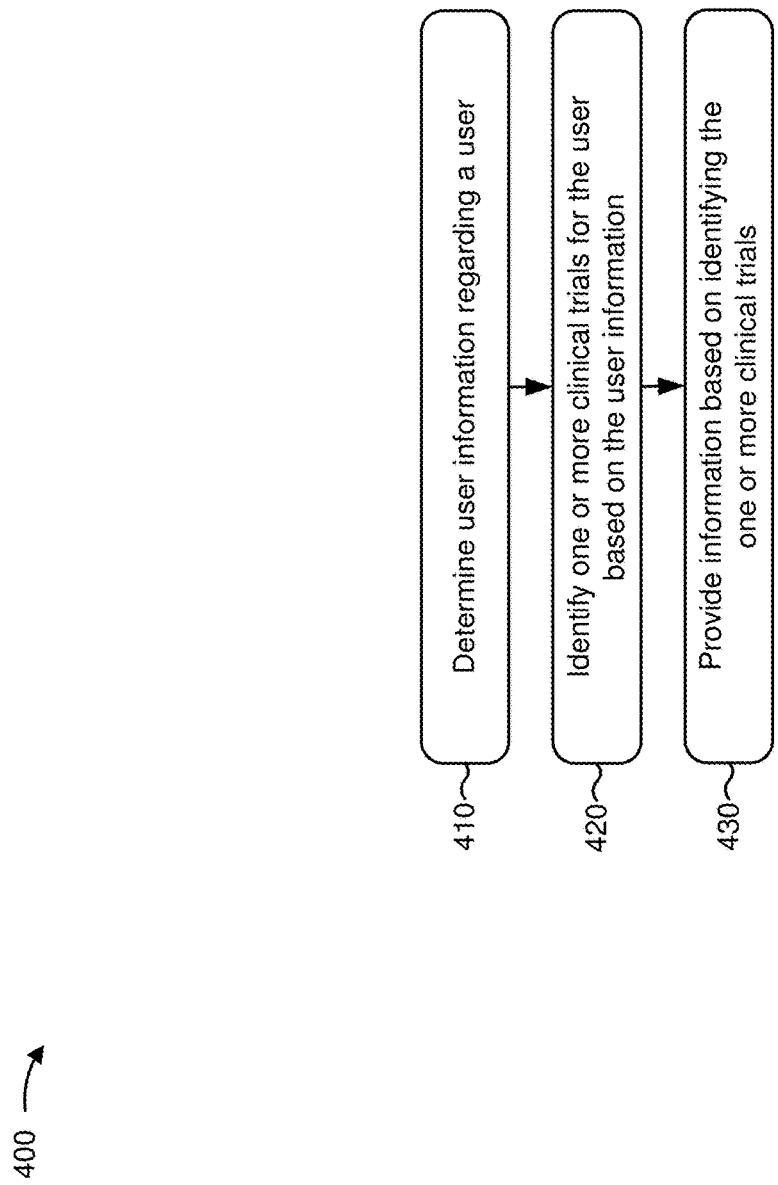
FIG. 4 is a flow chart of an example process for matching a user to a clinical trial.

FIG. 4 is a flow chart of an example process 400 for matching a user to a clinical trial. In some implementations, one or more process blocks of FIG. 4 may be performed by cloud server 220. In some implementations, one or more process blocks of FIG. 4 may be performed by another device or a group of devices separate from or including cloud server 220, such as user device 210.

As shown in FIG. 4, process 400 may include determining user information regarding a user (block 410). For example, cloud server 220 may determine user information associated with a user of user device 210. In some implementations, cloud server 220 may receive user information from user device 210. For example, cloud server 220 may cause a user interface, which includes one or more user interface elements with which to receive information input by a user, to be provided via user device 210. In this case, user device 210 may detect a user interaction with the user interface associated with inputting user information, and user device 210 may transmit an indication of the user information based on detecting the user interaction. In this way, cloud server 220 may permit a user (e.g., a potential participant in a clinical study) to provide user information to cloud server 220 based on interacting with one or more user interface elements of the user interface to cause cloud server 220 to match the user to a particular clinical study.

In some implementations, cloud server 220 may receive user information identifying a set of physical characteristics or mental characteristics associated with the user. For example, cloud server 220 may receive user information identifying a height, a weight, an age, a gender, a personality type, or the like. Additionally, or alternatively, cloud server 220 may receive user information associated with a medical history of the user, such as user information identifying a set of symptoms, a set of medications, a disease history, a family medical history, an allergen list, or the like. Additionally, or alternatively, cloud server 220 may receive user information relating to logistics of participation in a clinical trial by the user. For example, cloud server 220 may receive user information identifying a location of the user, a location of the user's place of employment, an insurance provider, an insurance plan, a desired travel range, a physical disability (e.g., paralysis, blindness, etc.), a time availability, or the like.

In some implementations, cloud server 220 may perform a data mining technique to determine user information. For example, cloud server 220 may perform a text analysis technique, a natural language processing technique, a heuristic technique, a matching technique, or the like to identify user information. In some implementations, cloud server 220 may perform data mining based on identifying a dataset associated with the user (after receiving permission from the user via the user interface to perform the data mining). For example, cloud server 220 may identify a user profile of a professional website (e.g., an employer website), a personal website (e.g., a blog), a medical website (e.g., an insurance provider's website), a social media account, or the like. In this case, cloud server 220 may determine user information based on extracting information from the dataset associated with the user. For example, based on a web search history, a web browser history, or the like, cloud server 220 may identify a symptom (e.g., a threshold quantity of searches for "cold medicine," "migraine relief," or the like). Similarly, based on a social media account including information identifying a set of locations visited by the user, cloud server 220 may identify potential diseases to which the patient has been exposed, a location at which the user is living, or the like. Additionally, or alternatively, cloud server 220 may continually or periodically monitor a user device 210 to determine user information. For example, cloud server 220 may monitor information associated with user device 210 (e.g., a message, a blog post, etc.) and may determine user information in real time or near real time based on the monitored information. In this way, user information associated with user device 210 may be updated more frequently relative to periodic updates, thereby providing more accurate user information of a user and improving the likelihood that the user is matched to a clinical trial that suits his/her qualifications.

In some implementations, cloud server 220 may identify a group (e.g., a social media group associated with a social media account of the user) associated with the user of user device 210, and may determine user information based on information associated with the group. For example, cloud server 220 may determine that user device 210 is operating an application associated with a particular group (e.g., a cancer support group application, a dietary program application, or the like), and may determine user information associated with the user based on information associated with the particular group (e.g., a cancer condition, a weight condition, etc.).

In some implementations, cloud server 220 may determine user information based on information available in a data structure. For example, cloud server 220 may access a medical or healthcare provider data structure, a government data structure, or the like (e.g., based on receiving appropriate permissions from the user via the user interface), and may determine information associated with the user of user device 210, such as medical information associated with the user, demographic information associated with the user, or the like. In this way, cloud server 220 may obtain user information regarding a user from one or more data sources. Moreover, based on automatically obtaining the user information based on performing a data mining technique or the like, cloud server 220 reduces an amount of time required to determine the user information relative to manual collection of user information, thereby reducing an amount of time required for cloud server 220 to match a user to a particular clinical trial and conserving processor resources. Similarly, cloud server 220 reduces a power usage associated with user device 210 by limiting the amount of user information that user device 210 provides to cloud server 220.

In some implementations, cloud server 220 may determine user information based on receiving sensor data (e.g., from user device 210). For example, cloud server 220 may cause user device 210 to perform one or more sensor observations, such as a motion sensor, a spirometer, a heartbeat sensor, a temperature sensor, a barometer, an accelerometer, or the like, and may process the sensor observations (e.g., via a processing technique, such as a data mining technique or a pattern recognition technique) to determine a suitability of a user for a particular clinical trial. Additionally, or alternatively, cloud server 220 may cause user device 210 to provide an instruction, for display, to cause a user to utilize a medical device, exercise equipment, or the like to obtain user information for utilization in matching the user to a clinical trial.

As further shown in FIG. 4, process 400 may include identifying one or more clinical trials for the user based on the user information (block 420). For example, cloud server 220 may identify one or more clinical trials for the user of user device 210 based on the determined user information. In some implementations, cloud server 220 may obtain information regarding a set of clinical trials from which to select the one or more clinical trials. For example, cloud server 220 may provide a user interface (e.g., via another user device 210) to receive information identifying a clinical trial from an investigator of the clinical trial (e.g., a doctor, a researcher, a clinician, etc.), a sponsor of the clinical trial (e.g., a hospital, an organization, a pharmaceutical company, etc.), or the like. Additionally, or alternatively, cloud server 220 may perform a data mining technique to obtain information identifying the set of clinical trials from which to select the one or more clinical trials. For example, cloud server 220 may perform an analysis of a government database storing information identifying clinical trials, a press release announcing a clinical trial, or the like.

In some implementations, cloud server 220 may identify a description of a particular clinical trial. For example, cloud server 220 may determine information identifying a title of the particular clinical trial, a condition being studied in the particular clinical trial, an intervention drug being utilized in the particular clinical trial, a set of objectives of the particular clinical trial, or the like. Additionally, or alternatively, cloud server 220 may determine a study size of the particular clinical trial, contact information for the particular clinical trial (e.g., contact information for an investigator, a sponsor, etc.), a set of requirements for a potential participant to be considered for acceptance into the particular clinical trial (e.g., a required disease, a required symptom, etc.), a set of participation criteria for a participant accepted into the clinical trial (e.g., a participant availability, a participant location, etc.), or the like.

In some implementations, cloud server 220 may obtain, for a particular clinical trial, information identifying a set of pre-screening criteria for presentation to a potential participant interested in the particular clinical trial. For example, pre-screening criteria may include a set of attributes that qualify a potential participant for a particular clinical trial (e.g., possessing a particular disease, utilizing a particular medication, living in a particular location, being a particular age, being a particular gender, having a particular medical history, possessing a particular insurance provider, or the like), that may not have been included in the user information. In some implementations, cloud server 220 may automatically determine an answer to one or more of the pre-screening criteria based on the user information, and may present a subset of the pre-screening criteria that cloud server 220 is unable to automatically answer. In this way, cloud server 220 reduces a quantity of memory resources utilized by user device 210 based on reducing a quantity of pre-screening criteria provided to user device 210. Moreover, cloud server 220 reduces a quantity of network traffic associated with sending messages between cloud server 220 and user device 210 via cloud network 230 based on reducing the quantity of pre-screening criteria sent via messages to user device 210.

In some implementations, cloud server 220 may identify one or more pre-screening criteria based on information available in a data structure storing clinical trial information (e.g., a medical database, a hospital database, a government database, or the like). For example, cloud server 220 may determine that a data structure storing information regarding a particular clinical trial includes a document identifying one or more pre-screening criteria. In some implementations, cloud server 220 may receive, from an investigator via user device 210, a questionnaire for the clinical trial which requests specific medical history information related to the particular clinical trial, specific logistical information related to the particular clinical trial, or the like.

In some implementations, cloud server 220 may automatically match the user of user device 210 to one or more clinical trials. For example, cloud server 220 may identify a set of attributes that qualify a potential participant for a particular clinical trial (e.g., possessing a particular symptom or the like) based on pre-screening criteria and may determine that the user is associated with the set of attributes for the particular clinical trial. In some implementations, cloud server 220 may determine a set of scores for the set of clinical trials associated with a suitability of the user for each clinical trial of the set of clinical trials. For example, cloud server 220 may determine the set of scores for the set of clinical trials using, for example, a scoring technique that measures how well information regarding the user (e.g., the user information, answers to the pre-screening criteria, etc.) matches the set of attributes for the particular clinical trial. Cloud server 220 may select the one or more clinical trials from the set of clinical trials based on a corresponding one or more scores for the one or more clinical trials. In this case, cloud server 220 may select the one or more clinical trials based on the corresponding one or more scores each satisfying a threshold value.

In another example, cloud server 220 may determine the set of scores for the set of clinical trials, and may select a threshold quantity of clinical trials associated with the highest scores relative to other scores of the set of scores. Similarly, cloud server 220 may select one or more clinical trials based on a score for a particular clinical trial, of the one or more clinical trials, being associated with a particular score percentile relative to other scores of the set of scores (e.g., top 5%, top 10%, top 20%, etc.). Similarly, cloud server 220 may select one or more clinical trials associated with one or more scores satisfying a threshold.

Additionally, or alternatively, cloud server 220 may select one or more clinical trials based on satisfying multiple criteria. For example, cloud server 220 may select a particular clinical trial based on a score for the particular clinical trial exceeding a particular threshold value and being associated with a particular score percentile relative to other scores of the set of scores.

In this way, cloud server 220 may reduce a quantity of memory resources required to store information for presentation to the user based on selecting the one or more clinical trials from the set of clinical trials relative to storing information regarding each clinical trial of the set of clinical trials.

In some implementations, cloud server 220 may identify a particular clinical trial, of the one or more clinical trials, based on identifying a partial match between a set of attributes of the user and a set of attributes of the particular clinical trial. For example, cloud server 220 may determine, based on the user information and/or information regarding the particular clinical trial, that the user satisfies a threshold quantity of attributes required for participation in the particular clinical trial, and may include the particular clinical trial in the one or more clinical trials despite the user failing to satisfy all attributes required for participation. In this way, cloud server 220 may permit matching of participants to clinical trials with flexible participation requirements.

As further shown in FIG. 4, process 400 may include providing information based on identifying the one or more clinical trials (block 430). For example, cloud server 220 may provide information to user device 210 based on identifying the one or more clinical trials. In some implementations, cloud server 220 may generate a user interface for presentation via user device 210. For example, cloud server 220 may generate a user interface that includes information identifying a clinical trial description, a clinical trial location, a clinical trial testing date a clinical trial pre-screening questionnaire, or the like, and may cause the user interface to be provided for display via user device 210.

In some implementations, cloud server 220 may receive a selection of a particular clinical trial of the one or more clinical trials based on providing the information identifying the one or more clinical trials. For example, cloud server 220 may receive, via the user interface, a selection of the particular clinical trial, and may perform one or more response actions based on receiving the selection of the particular clinical trial, such as providing additional information regarding the particular clinical trial, providing a pre-screening questionnaire associated with the particular clinical trial, or the like.

In some implementations, cloud server 220 may automatically generate a calendar entry for a calendar associated with user device 210 to provide information based on identifying the one or more clinical trials. For example, cloud server 220 may obtain calendar information associated with the user and/or an investigator conducting the clinical trial, and may schedule a meeting for the user and the investigator conducting the clinical trial, and may cause a calendar entry identifying a date and time of the meeting to be provided to the user via a first user device 210, to the investigator via a second user device 210, or the like.

Additionally, or alternatively, cloud server 220 may automatically register the user for a particular clinical trial, of the one or more clinical trials, and may perform monitoring for the particular clinical trial, such as monitoring a medication schedule, an exercise schedule, an appointment schedule, or the like. For example, cloud server 220 may provide reminders to perform activities related to preparing the user for the clinical trial (e.g., a reminder to take medicine for the clinical trial, a reminder to exercise for the clinical trial, a reminder to fast for the clinical trial, a reminder to drink fluids for the clinical trial, or the like). In this way, a qualified user may be notified automatically when they are matched to a potential clinical trial and begin actions related to preparing for the clinical trial immediately.

In some implementations, cloud server 220 may provide information to an investigator performing a particular clinical trial of the one or more clinical trials. For example, cloud server 220 may provide information identifying the user, such as contact information, medical information, availability information, or the like to an investigator (e.g., via a user interface of user device 210) based on the user consenting to release of the information. In this way, cloud server 220 permits the investigator to identify a greater quantity of potential participants for the clinical trial relative to relying on word of mouth or advertisements.

Additionally, or alternatively, cloud server 220 may provide analytics information based on identifying the one or more clinical trials. For example, cloud server 220 may provide information specifying locations where a threshold quantity of users, who are qualified for a particular clinical trial of the one or more clinical trials, are located. In this way, cloud server 220 may assist investigators in selecting at which hospital to conduct the particular clinical trial. In another example, cloud server 220 may automatically select a hospital at which to conduct a particular clinical trial based on identifying a location at which a threshold quantity of users who qualify for the particular clinical trial are located.

In some implementations, cloud server 220 may provide tracking information related to a particular clinical trial. For example, cloud server 220 may provide, to an investigator, information identifying a quantity of users that access a description of a particular clinical trial, track how often users share information regarding a particular clinical trial, or the like. In this way, cloud server 220 may provide information related to potential participants' interests in a particular clinical trial, thereby allowing an investigator conducting the clinical trial to determine an effectiveness of an advertising campaign associated with the clinical trial.

In some implementations, cloud server 220 may provide tracking information associated with identifying a set of criteria based on which a particular potential participant was matched for a particular clinical trial. For example, cloud server 220 may provide information relating to a set of attributes identified for the potential participant and a set of attributes identified for the particular clinical trial, information identifying a participant's score for the particular clinical trial, or the like. In this way, a potential participant may alter his/her user information to find clinical trials that better match a participant's preferences based on the tracking information provided by cloud server 220. In some implementations, cloud server 220 may provide information associated with identifying a characteristic of a potential participant's application for a particular clinical trial. For example, cloud server 220 may provide a date and a time at which a potential participant applied for a particular clinical trial, a type of user device 210 that was utilized, when the participant was matched to the particular clinical trial, when the participant answered a pre-screening questionnaire associated with the particular clinical trial, or the like. In this way, cloud server 220 may provide an investigator conducting a clinical trial with tracking information related to other clinical trials, thereby providing the investigator with information for determining a duration of time that a trial may be available for potential participants to apply in order to achieve a maximum number of participants.

In some implementations, cloud server 220 may automatically enroll a potential participant in a particular clinical trial based on the potential participant's determined user information. For example, cloud server 220 may determine user information associated with each user of a set of users, determine a score for each user of the set of users, and provide information indicating the selection of a particular user for a particular clinical trial based on the determined score. In this case, cloud server 220 may automatically provide a user with information relating to enrolling in the particular clinical trial (e.g., information identifying a description of the particular clinical trial, a scheduled meeting with an investigator conducting the particular clinical trial, a pre-screening questionnaire to complete, or the like) based on selecting the particular user for the particular clinical trial. In this way, cloud server 220 may automatically find a clinical trial for a user, thereby reducing an amount of time associated with searching for a clinical trial relative to utilizing manual searches.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

FIGS. 5A-5F are diagrams of an example implementation 500 relating to example process 400 shown in FIG. 4. FIGS. 5A-5F show an example of matching a user to a clinical trial.

Figures 5A, 5B:
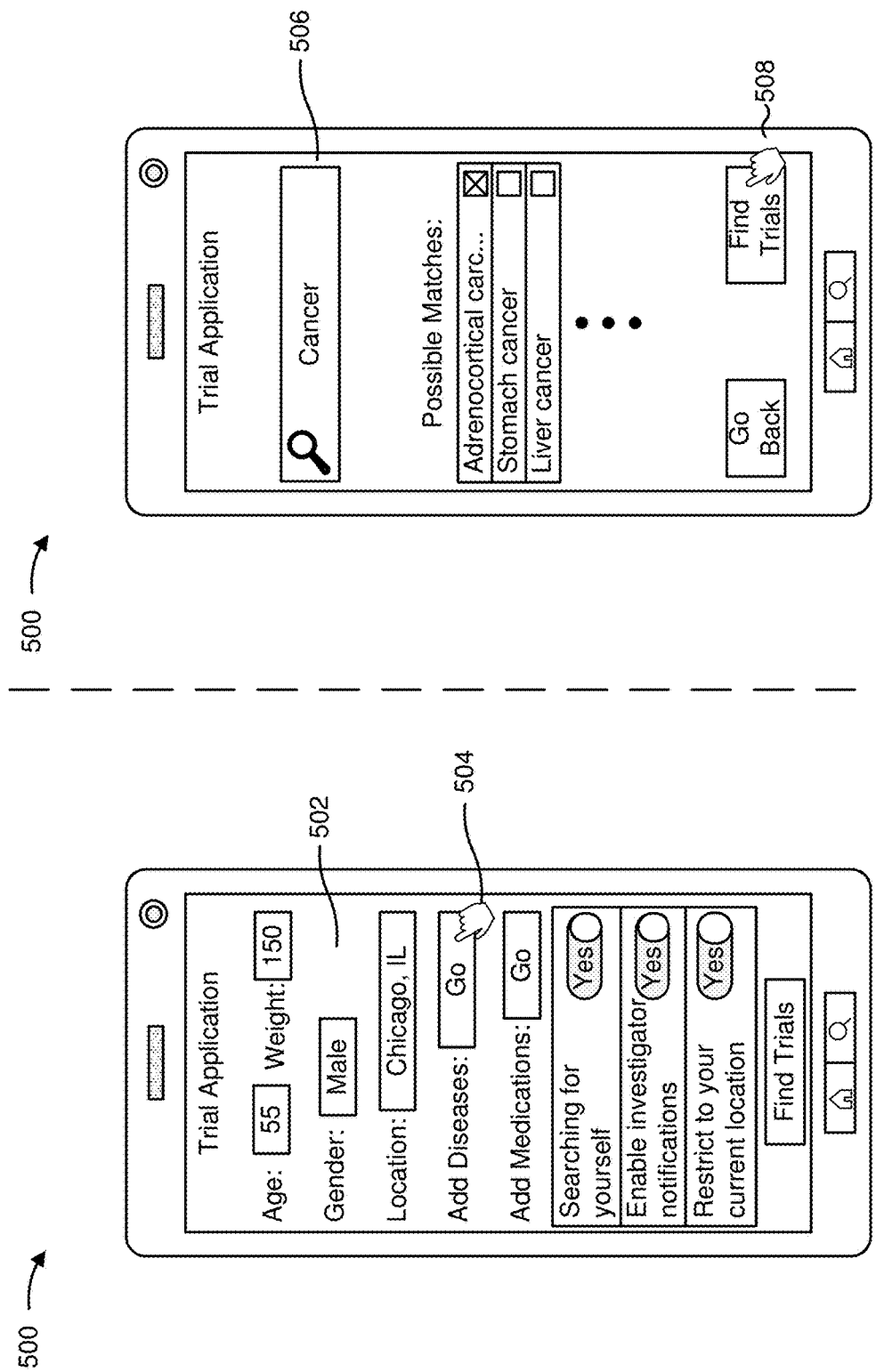

As shown in FIG. 5A, a cloud server 220 provides, via user device 210, a user interface with which to determine user information. As shown by reference number 502, cloud server 220 provides a set of user interface elements (e.g., a set of text-entry boxes) that are utilized to receive user information, such as a user age, a user weight, a user location (e.g., which may be automatically determined based on location information associated with user device 210), a set of user diseases, a set of user medications, or the like. Similarly, cloud server 220 provides a set of user interface elements with which to receive a selection of whether the user is searching for a clinical trial for the user or on behalf of another user, whether the user desires to receive notifications from an investigator of the clinical trial, whether the user desires to restrict the clinical trial search results to a location near the user, or the like. In another example, when the user indicates a desire to search for clinical trials on behalf of another person, cloud server 220 may request additional user information (e.g., relating to the other user) before identifying one or more clinical trials matching the user information. As shown by reference number 504, based on user interaction with a button, cloud server 220 may be caused to provide another presentation of the user interface with which to add a disease to the user information.

As shown in FIG. 5B, cloud server 220 provides, via user device 210, a user interface with which to identify a disease for the user information. As shown by reference number 506, a user may search for a particular disease via a search bar user interface. As shown, cloud server 220 may provide an indication of a set of diseases matching the search. Assume that based on a user interaction with a checkbox, the user indicates that a particular disease is to be added to the user information. As shown by reference number 508, based on user interaction with a button, cloud server 220 is caused to provide information identifying one or more clinical trials for which the user is qualified based on the user information.

As shown in FIG. 5C, cloud server 220 provides, via user device 210, a user interface to identify particular information about a particular clinical trial for which the user is qualified based on the user information. As shown by reference number 510, cloud server 220 includes information identifying the clinical trial (e.g., a title, a condition being studied, a medication being tested, a location of the clinical trial, etc.). As shown by reference number 512, cloud server 220 provides a set of user interface elements permitting the user to be provided with additional information regarding the clinical trial (e.g., a brief summary of the clinical trial, participation criteria, contact information, etc.). In this way, a user may determine if the user desires to apply for the clinical trial based on the clinical trial information. As shown by reference number 514, based on an interaction with a button, a user interested in applying for a clinical trial may cause cloud server 220 to add the clinical trial to a list of clinical trials to which the user is to apply.

As shown in FIG. 5D, cloud server 220 provides, via user device 210, a user interface including a list of clinical trials to which the user is to apply. The user may cause cloud server 220 to add additional trials to the list based on interacting with the "Find Trials" button. As shown by reference number 518, based on an interaction with the "Go To Dashboard" button, cloud server 220 is caused to provide a dashboard view user interface.

Figure 5E:
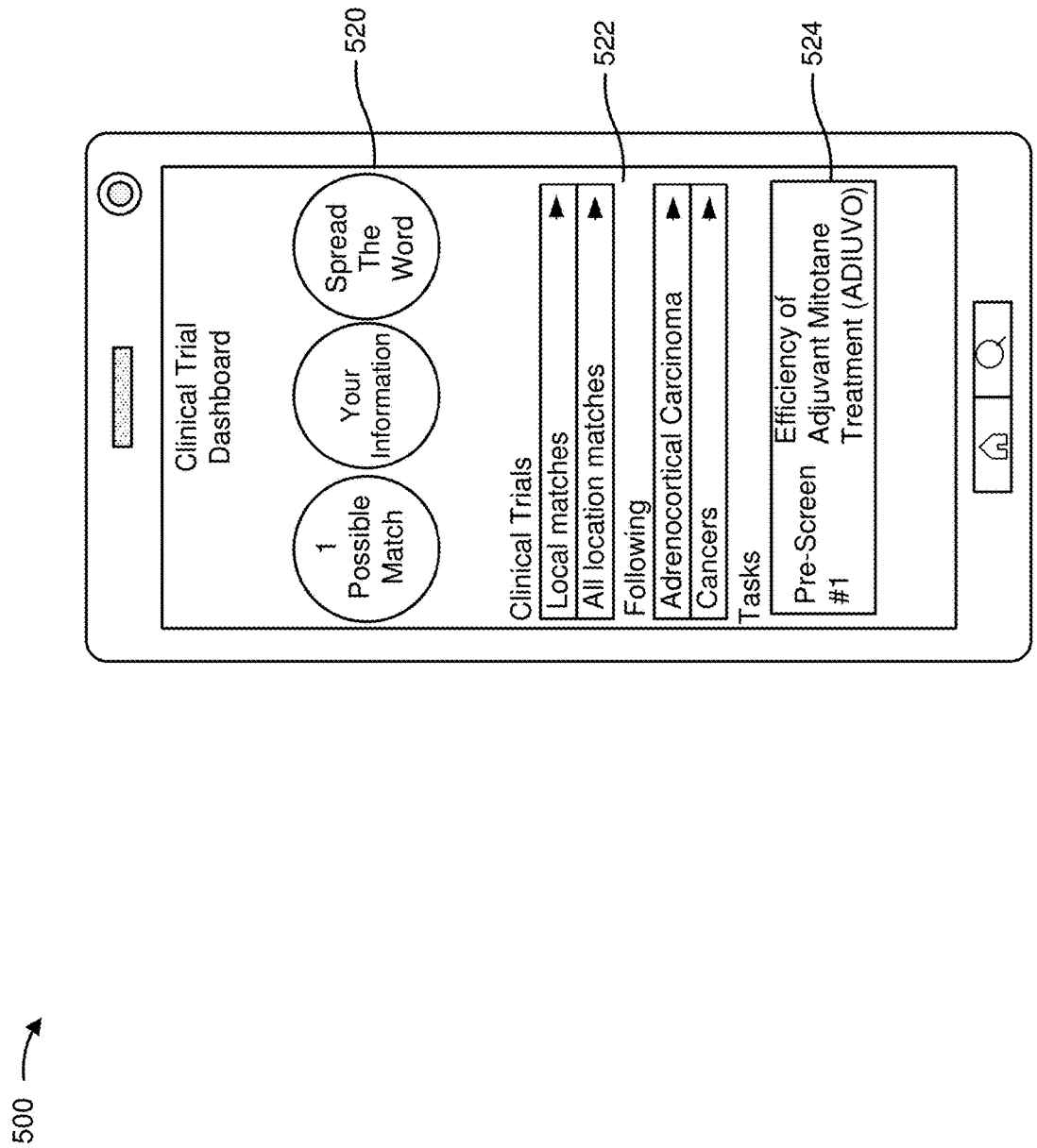

As shown in FIG. 5E, cloud server 220 provides dashboard view user interface. As shown by reference number 520, cloud server 220 provides user interface elements to permit the user to view the list of clinical trials, edit the user information, and share clinical trial information with others. For example, the user of user device 210 may be associated with a social media group associated with Adrenocortical Carcinoma and may automatically cause cloud server 220 to share the trial with the social media group. In this way, cloud server 220 may permit clinical trial information to be viewed by users likely to be interested in the clinical trial information, thereby reducing a quantity of messages transmitted to advertise the clinical trial and/or a quantity of processing and/or memory resources associated with storing and displaying the clinical trial information relative to providing the clinical trial information to every available user. As shown by reference number 522, cloud server 220 provides a user interface element permitting a search for one or more additional clinical trials (e.g., local clinical trials, non-local clinical trials, etc.). Similarly, cloud server 220 may provide a user interface element permitting the user to be provided with information regarding a user disease (e.g., Adrenocortical carcinoma, cancer, or the like), such as additional clinical trials that are announced, news articles relating to the user disease, or the like. In this way, cloud server 220 may automatically provide information relevant to the user's medical condition and desire to participate in clinical trials, thereby obviating the need for the user to perform manual searches for information and reducing a quantity of network traffic relative to the user performing manual searches for information. As shown by reference number 524, cloud server 220 may provide information identifying one or more tasks to be completed for user participation in and/or application for a particular clinical trial. For example, cloud server 220 may provide a user interface element for receiving a request to be provided a pre-screening questionnaire regarding the user for participation in the clinical trial. Assume the user selects to be provided the pre-screening questionnaire.

Figure 5F:
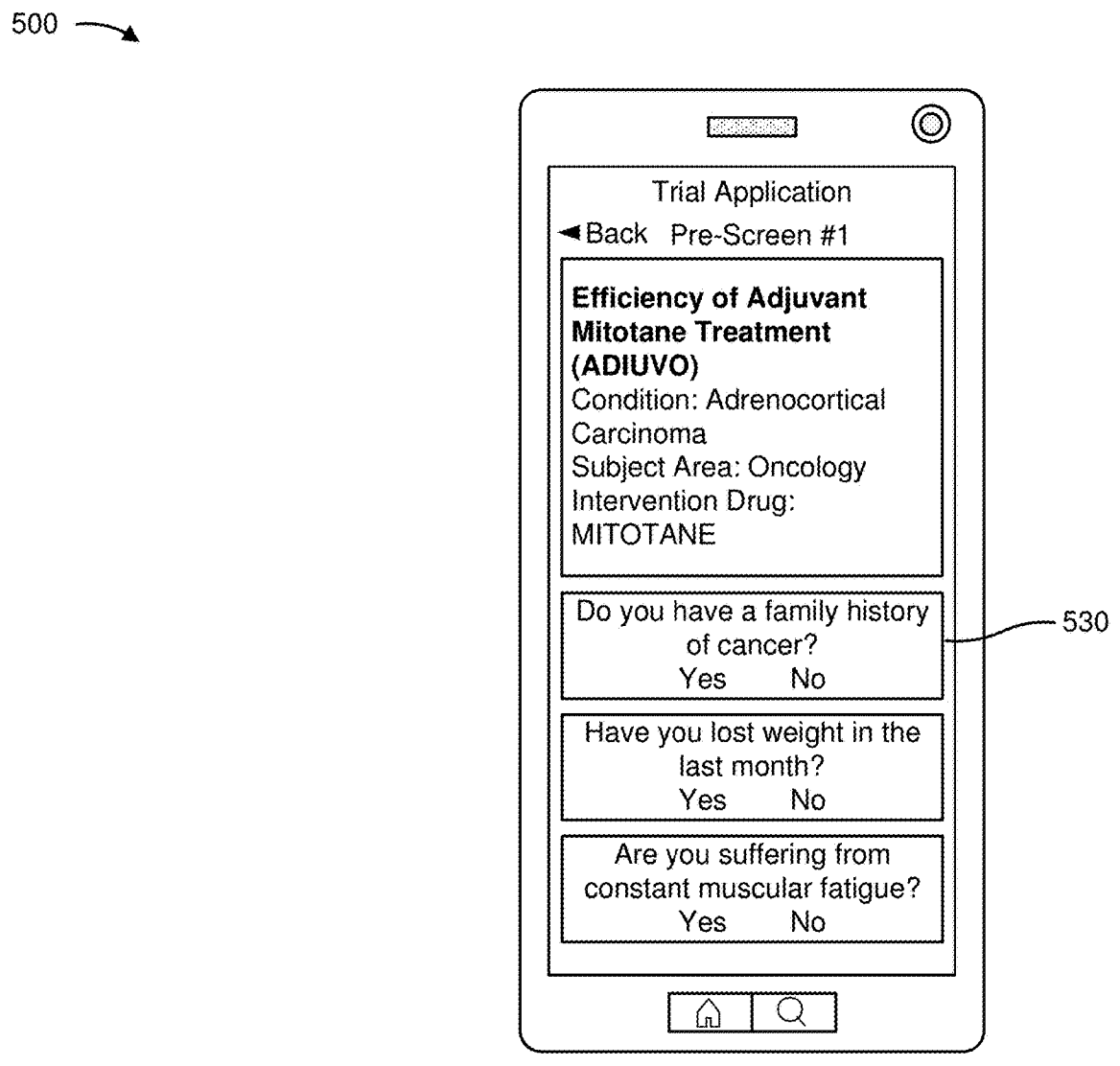

As shown in FIG. 5F, cloud server 220 provides, via user device 210, a user interface displaying pre-screening questionnaire prompts related to the clinical trial. As shown by reference number 530, cloud server 220 provides a set of user interface elements for identifying prompts of the pre-screening questionnaire and for receiving responses to the prompts. In this way, cloud server 220 may provide an investigator with detailed medical and logistical information needed to choose qualified participants for a clinical trial.

As indicated above, FIGS. 5A-5F are provided merely as an example. Other examples are possible and may differ from what was described with regard to FIGS. 5A-5F.

Figure 6A:
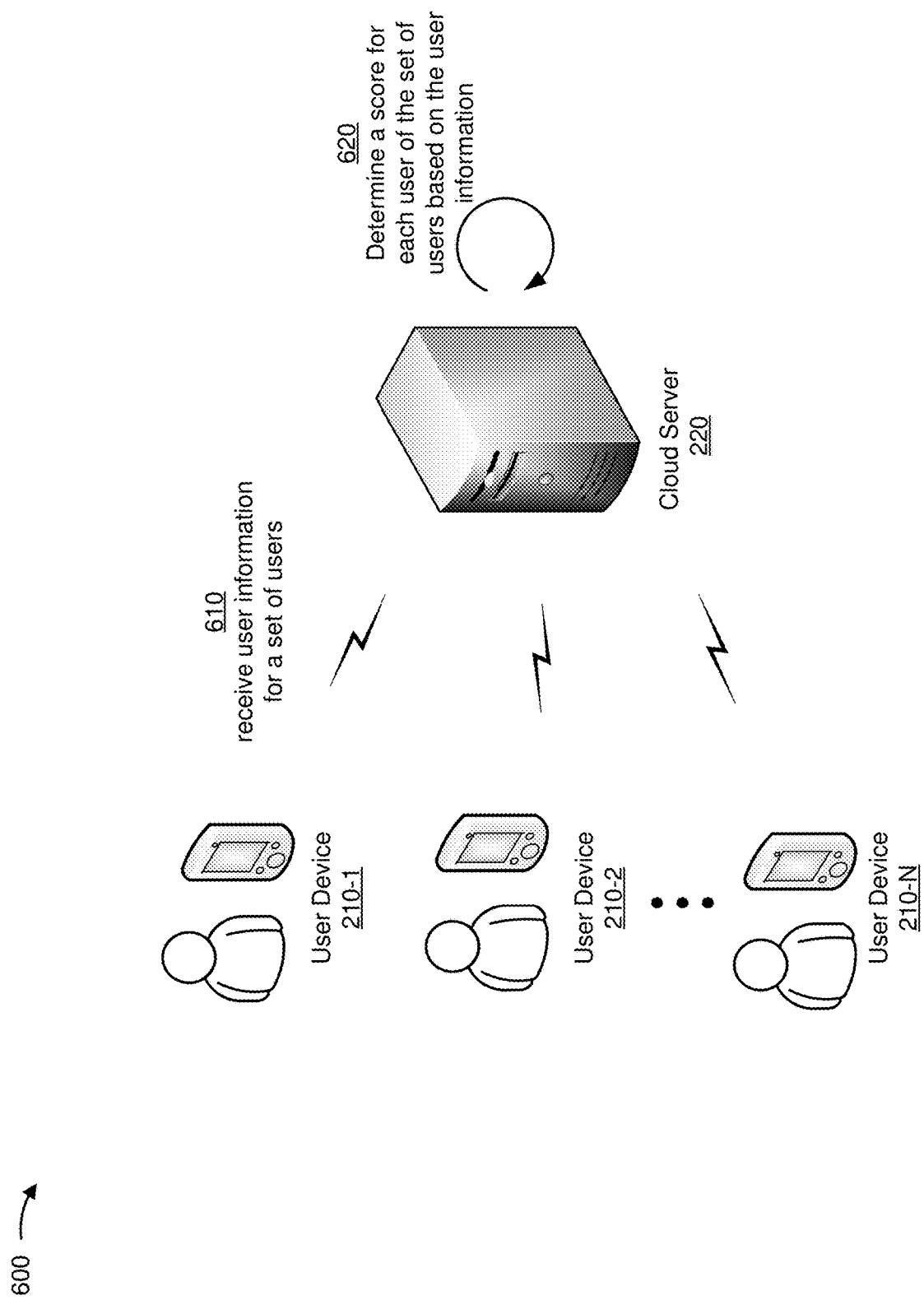
Figure 6C:
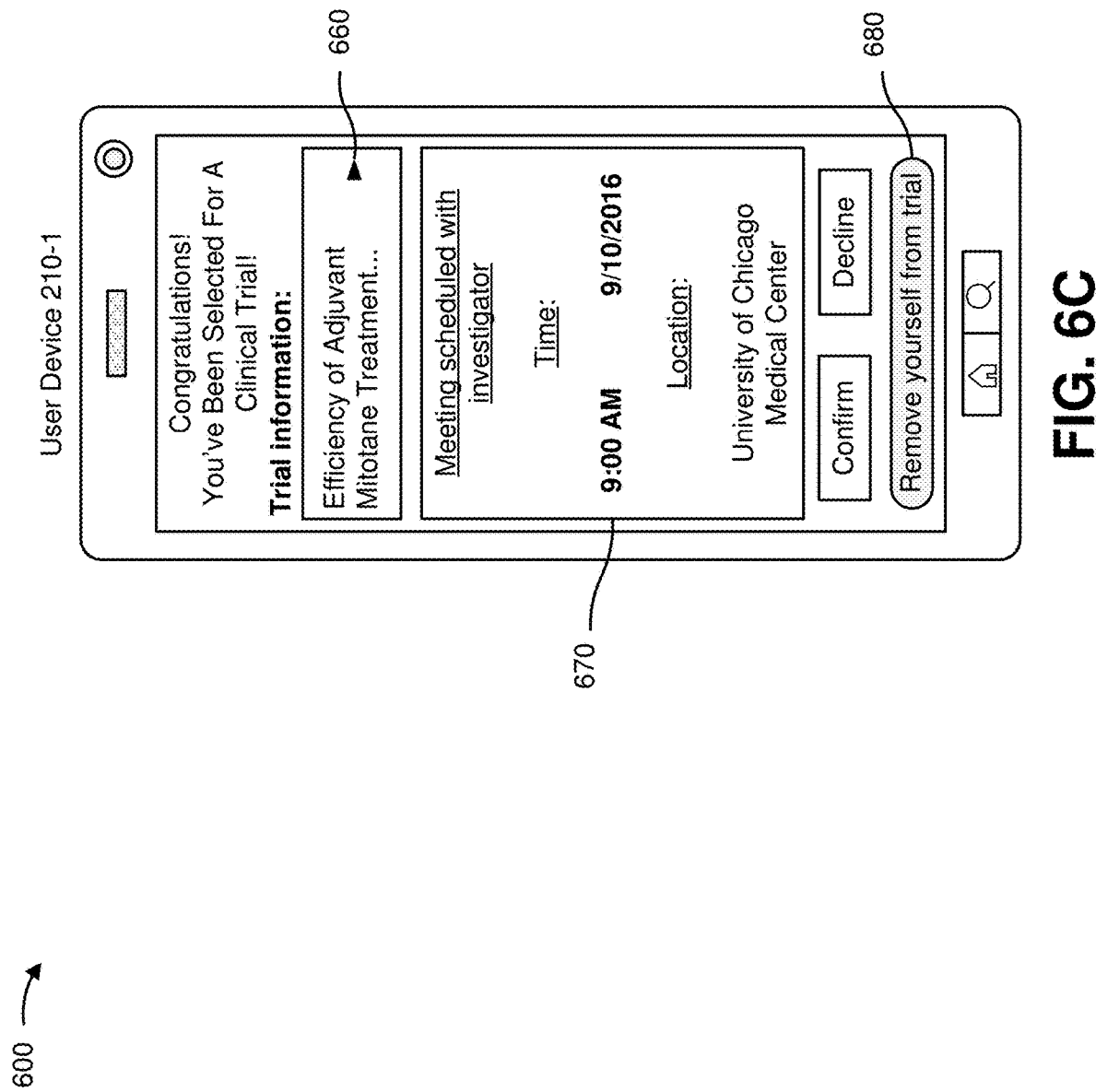

FIGS. 6A-6C are diagrams of an example implementation 600 relating to example process 400 shown in FIG. 4. FIGS. 6A-6C show an example of automatically matching a user to a clinical trial.

As shown in FIG. 6A, cloud server 220 and by reference number 610, cloud server 220 receives, from each user device 210 of a set of user devices 210, user information relating to a potential participant for a particular clinical trial (e.g., a user of a corresponding user device 210). For example, cloud server 220 may receive medical information (e.g., a symptom, an age, a gender, or the like) and/or logistical information (e.g., a location, a desired travel range, or the like) for each user of a set of users. As shown by reference number 620, cloud server 220 utilizes a matching technique to determine a score for each user of the set of users. For example, cloud server 220 may compare a first set of attributes associated with the particular clinical trial with a second set of attributes associated with a particular user, and may generate a score based on the comparison. In this way, cloud server 220 may reduce processing resources utilized by user device 210 by automatically providing a matching score for a particular clinical trial relative to user device 210 searching for clinical trials that match a potential participant's user information.

As shown in FIG. 6B, and by reference number 630, cloud server 220 selects a user, of the set of users, for participation in the clinical trial based on the set of scores. For example, assume that a user may be accepted for a clinical trial based on receiving a score satisfying a particular threshold value (e.g., 90). Additionally, or alternatively, the user may be determined to satisfy a set of acceptance criteria, and may be invited to proceed further with being selected for the clinical trial. As shown by reference number 640, cloud server 220 provides information to users not selected for the particular clinical trial (e.g., based on being associated with scores failing to exceed the particular threshold value) indicating that the users are not selected. For example, cloud server 220 may provide the information to user device 210-2 and user device 210-N (e.g., associated with respective scores of 68 and 75). In this way, cloud server 220 may reduce a memory resource associated with user device 210 by indicating that a corresponding user is not selected for the particular clinical trial thereby permitting user device 210 to refrain from storing information relating to the particular clinical trial. As shown by reference number 650, cloud server 220 provides, to user device 210-1, information indicating a selection for the particular clinical trial based on a score associated with user device 210-1 (e.g., 93) exceeding the particular threshold value.

As shown in FIG. 6C, cloud server 220 provides, via a user interface of user device 210-1, information relating to the clinical trial in which the user of user device 210-1 is selected to participate. As shown by reference number 660, cloud server 220 provides information associated with identifying the particular clinical trial (e.g., a clinical trial title, a clinical trial description, or the like). As shown by reference number 670, cloud server 220 provides information identifying a meeting scheduled for the user with an investigator conducting the clinical trial. For example, cloud server 220 provides information identifying a time and a location for the meeting and user interface elements to receive a confirmation of attendance of the meeting. As shown by reference number 680, cloud server 220 may provide a user interface element to receive a selection to remove the user from participation in the clinical trial. For example, when a user does not desire to participate in the clinical trial to which the user was automatically matched, the user may interact with user device 210-1 to cause a removal from the clinical trial participants. In another example, user device 210-1 may provide, for display, information associated with the clinical trial to facilitate obtaining informed consent for the clinical trial. For example, user device 210-1 may provide a disclosure statement, a legal statement, or the like, and may receive input associated with indicating consent, and may transmit an indication of consent to a server device associated with administration of the clinical trial.

As indicated above, FIGS. 6A-6C are provided merely as an example. Other examples are possible and may differ from what was described with regard to FIGS. 6A-6C.

Implementations, described herein, relate to matching a potential participant to one or more clinical trials of a set of clinical trials. Matching potential participants to clinical trials may improve the opportunity for potential participants to participate in clinical trials. Additionally, or alternatively, matching potential participants to clinical trials may enable investigators to conduct trials more easily relative to seeking participation through other techniques.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

Certain user interfaces have been described herein and/or shown in the figures. A user interface may include a graphical user interface, a non-graphical user interface, a text-based user interface, etc. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code-it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A non-transitory computer-readable medium storing instructions, the instructions comprising:
   one or more instructions that, when executed by one or more processors, cause the one or more processors to:
   obtain, from a first device, first data regarding a set of events,
      the first data including pre-screening criteria for a particular event of the set of events;
   obtain, from a second device, second data regarding a user,
      the second data including:
         a web search history,
         a web browser history, and
         social media account information;
   receive, from one or more sensors of the second device, sensor data;
   perform a data mining technique on the second data and the sensor data to determine user information,
      the user information including at least one of:
         a potential symptom of the user,
         a potential disease to which the user has been exposed, or
         a particular condition of the user other than the potential symptom and the potential disease;
   automatically determine, based on the user information, one or more answers to a first subset of the pre-screening criteria for the particular event;
   determine, based on the user information, a set of scores for the set of events,
      each score, of the set of scores, being associated with a corresponding event of the set of events and indicating how well the user information matches a set of attributes for the corresponding event, and
      a particular score, of the set of scores, for the particular event being determined based on the one or more answers to the first subset of the pre-screening criteria;
   select the particular event based on the particular score satisfying a threshold value;
   provide, via a first user interface, a set of user interface elements relating to participation in the particular event,
      the first user interface being a dashboard view user interface, and
      the set of user interface elements including:
         a first user interface element configured to initiate, upon selection, a set of prompts relating to a second subset of the pre-screening criteria for which one or more answers were not automatically determined, and
         a second user interface element configured to enable, upon selection, information regarding the particular event to be shared with another device;
   provide, via a second user interface and based on the first user interface element being selected, the set of prompts,
      the set of prompts, including a questionnaire;
   detect an interaction with the second user interface associated with responding to the set of prompts;
   provide, to an investigator associated with the particular event, information identifying the user based on the interaction with the second user interface associated with responding to the set of prompts;
   provide, to the other device and based on the second user interface element being selected, the information regarding the particular event;
   obtain first calendar information associated with the user and second calendar information associated with the investigator;
   identify a meeting time and a meeting location for the user and the investigator based on the first calendar information and the second calendar information; and
   cause a first calendar entry to be included in a first calendar associated with the user and a second calendar entry to be included in a second calendar associated with the investigator,
      the first calendar entry and the second calendar entry identifying the meeting time and the meeting location.

2. The non-transitory computer-readable medium of claim 1, where the one or more instructions, when executed by the one or more processors, further cause the one or more processors to:
  identify a set of responses to the set of prompts based on detecting the interaction with the second user interface; and
  determine that the set of responses satisfy the second subset of the pre-screening criteria; and
  where the one or more instructions, that cause the one or more processors to provide the information identifying the user, cause the one or more processors to:
    provide the information identifying the user based on determining that the set of responses satisfy the second subset of the pre-screening criteria.

3. The non-transitory computer-readable medium of claim 1, where the one or more instructions, when executed by the one or more processors, further cause the one or more processors to:
  identify one or more data sources storing information regarding the user,
    the one or more data sources including the first device; and
  perform the data mining technique on data stored via the one or more data sources; and
  where the one or more instructions, that cause the one or more processors to obtain, from the first device, the first data regarding set of events, cause the one or more processors to:
    obtain the first data regarding the set of events based on performing the data mining technique on the data stored via the one or more data sources.

4. The non-transitory computer-readable medium of claim 3, where the one or more instructions, that cause the one or more processors to identify the one or more data sources, cause the one or more processors to:
  identify at least one of:
    a healthcare provider data structure,
    a government data structure, or
    one or more sensor devices.

5. The non-transitory computer-readable medium of claim 1, where the one or more instructions, when executed by the one or more processors, further cause the one or more processors to:
  identify a first set of attributes associated with the particular event based on the first data;
  identify a second set of attributes associated with the user based on the second data;
  compare the first set of attributes and the second set of attributes to determine the particular score; and
  provide information identifying the particular event based on the particular score; and
  where the one or more instructions, that cause the one or more processors to select the particular event, are further to:
    select the particular event based on providing the information identifying the particular event.

6. The non-transitory computer-readable medium of claim 1, where the set of events is a set of clinical trials and the particular event is a particular clinical trial; and
  where the one or more instructions, that cause the one or more processors to provide the information identifying the user, cause the one or more processors to:
    provide the information identifying the user to automatically enroll the user in the particular clinical trial.

7. A device, comprising:
  a memory; and
  one or more processors to:
    obtain data regarding a user,
      the data including:
        a web search history,
        a web browser history, and
        social media account information;
    receive, from one or more sensors of a first device associated with the user, sensor data;
    perform a data mining technique on the data and the sensor data to determine user information regarding the user,
      the user information including at least one of:
        a potential symptom of the user,
        a potential disease to which the user has been exposed, or
        a particular condition of the user other than the potential symptom and the potential disease;
    determine, based on the user information, a set of scores for a set of potential clinical trials,
      each score, of the set of scores, being associated with a corresponding clinical trial of the set of potential clinical trials and indicating how well the user information matches a set of attributes for the corresponding clinical trial;
    identify one or more clinical trials, of the set of potential clinical trials, for the user based on one or more scores, of the set of scores, associated with the one or more clinical trials satisfying a threshold value;
    provide, for display via the first device, information identifying the one or more clinical trials based on identifying the one or more clinical trials for the user;
    receive, via a first user interface at the first device and based on providing the information identifying the one or more clinical trials, a selection of a particular clinical trial of the one or more clinical trials;
    automatically determine, based on the user information, one or more answers to a first subset of pre-screening criteria for the particular clinical trial;
    provide, via a second user interface at the first device, a set of user interface elements relating to participation in the particular clinical trial,
      the second user interface being a dashboard view user interface, and
      the set of user interface elements including:
        a user interface element configured to initiate, upon selection, a set of prompts relating a second subset of the pre-screening criteria for which one or more answers were not automatically determined;
    provide, via a third user interface at the first device and based on the user interface element being selected, the set of prompts,
      the set of prompts including a questionnaire;
    provide, for display via a second device associated with an investigator of the particular clinical trial, information associated with responses to the set of prompts; and
    at least one of:
      register the user for the particular clinical trial,
      monitor the particular clinical trial, or
      enroll the user for the particular clinical trial.

8. The device of claim 7, where the one or more processors are further to:
  receive, from the second device associated with the investigator, information regarding the particular clinical trial; and
  where the one or more processors, when identifying the one or more clinical trials, are to:
    identify the particular clinical trial based on receiving the information regarding the particular clinical trial.
9. The device of claim 7, where the one or more processors are further to:
  receive, from the first device, information indicating that the user satisfies the pre-screening criteria; and
  where the one or more processors, when providing the information associated with the responses to the set of prompts, are to:
    provide the information associated with the responses to the set of prompts based on receiving the information indicating that the user satisfies the pre-screening criteria.
10. The device of claim 7, where the one or more processors are further to:
  determine, based on a matching technique, that a particular pre-screening criterion, of the pre-screening criteria, associated with the particular clinical trial is satisfied based on the user information; and
  omit the particular pre-screening criterion from the pre-screening criteria.
11. The device of claim 7, where the data is first data;
  where the one or more processors are further to:
    identify one or more social media groups with which the user is associated,
      the one or more social media groups containing the user information stored in a data structure; and
    perform the data mining technique on second data stored via one or more social media groups; and
  where the one or more processors, when determining the user information, are to:
    determine the user information based on performing the data mining technique on the second data stored via one or more social media groups.
12. The device of claim 7, where the one or more processors are further to:
  receive, from the second device, information identifying the particular clinical trial;
  add the particular clinical trial to the set of potential clinical trials based on receiving the information identifying the particular clinical trial; and
  where the one or more processors, when identifying the one or more clinical trials, are to:
    identify the one or more clinical trials after adding the particular clinical trial to the set of potential clinical trials.
13. The device of claim 7, where the one or more sensors include one or more of:
  a motion sensor,
  a spirometer,
  a heartbeat sensor,
  a temperature sensor,
  a barometer, or
  an accelerometer.
14. A method, comprising:
  obtaining, by a first device, data regarding a user,
    the data including:
      a web search history,
      a web browser history, and
      social media account information;
  receiving, by the first device and from one or more sensors of a second device, sensor data;
  performing, by the first device, a data mining technique on the data and the sensor data to determine user information regarding the user,
    the user being a potential participant in a clinical trial, and
    the user information including at least one of:
      a potential symptom of the user,
      a potential disease to which the user has been exposed, or
      a particular condition of the user other than the potential symptom and the potential disease;
  determining, by the first device, information associated with a set of clinical trials,
    the information associated with the set of clinical trials including pre-screening criteria for a particular clinical trial of the set of clinical trials;
  automatically determining, by the first device and based on the user information, one or more answers to a first subset of the pre-screening criteria for the particular clinical trial;
  comparing, by the first device, the user information and the information associated with the set of clinical trials;
  generating, by the first device, a set of scores for the set of clinical trials based on comparing the user information and the information associated with the set of clinical trials,
    each score, of the set of scores, being associated with a corresponding clinical trial of the set of clinical trials and indicating how well the user information matches a set of attributes for the corresponding clinical trial, and
    a particular score, of the set of scores, for the particular clinical trial being determined based on the one or more answers to the first subset of the pre-screening criteria;
  selecting, by the first device, the particular clinical trial based on the particular score satisfying a threshold value;
  providing, by the first device and via a first user interface based on selecting the particular clinical trial, a set of user interface elements relating to participation in the particular clinical trial,
    the first user interface being a dashboard view user interface, and
    the set of user interface elements including:
      a first user interface element configured to initiate, upon selection, a set of prompts relating to a second subset of the pre-screening criteria for which one or more answers were not automatically determined, and
      a second user interface element configured to enable, upon selection, information regarding the particular clinical trial to be shared to another device;
  providing, by the first device via a second user interface and based on the first user interface element being selected, the set of prompts,
    the set of prompts including a questionnaire;
  detecting, by the first device, an interaction with the second user interface associated with responding to the set of prompts;
  providing, by the first device and to a third device based on the interaction with the second user interface associated with responding to the set of prompts, information associated with responses to the set of prompts; and providing, by the first device and to a fourth device based on the second user interface element being selected, the information regarding the particular clinical trial.

15. The method of claim 14, further comprising:
matching the user to a plurality of clinical trials, of the set of clinical trials, based on the set of scores,
the plurality of clinical trials including the particular clinical trial;
providing, via a third user interface, information identifying the plurality of clinical trials;
detecting a selection of the particular clinical trial; and
providing the information regarding the particular clinical trial based on detecting the selection of the particular clinical trial.

16. The method of claim 14, further comprising:
obtaining first calendar information associated with the user and second calendar information associated with an investigator associated with the particular clinical trial;
identifying a meeting time and a meeting location for the user and the investigator based on the first calendar information and the second calendar information; and
causing a first calendar entry to be included in a first calendar associated with the user and a second calendar entry to be included in a second calendar associated with the investigator,
the first calendar entry and the second calendar entry identifying the meeting time and the meeting location.

17. The method of claim 14, further comprising:
identifying a first set of attributes associated with the user based on the user information;
identifying a second set of attributes associated with the particular clinical trial based on the information associated with the set of clinical trials; and
determining that the first set of attributes at least partially matches the second set of attributes; and
where selecting the particular clinical trial comprises:
selecting the particular clinical trial based on determining that the first set of attributes at least partially matches the second set of attributes.

18. The method of claim 17, further comprising:
determining the particular score based on comparing the first set of attributes with the second set of attributes; and
determining that the particular score satisfies the threshold value; and
where determining that the first set of attributes at least partially matches the second set of attributes comprises:
determining that the first set of attributes at least partially matches the second set of attributes based on determining that the particular score satisfies the threshold value.

19. The method of claim 14, further comprising:
providing, via a third user interface, a third user interface element indicating that the user is to be removed from participation in the particular clinical trial.

20. The method of claim 14, where the data is first data;
where the method further comprises:
displaying an instruction to cause the user to utilize at least one of a medical device or exercise equipment; and
where performing the data mining technique to determine the user information comprises:
performing the data mining technique on second data received from at least one of the medical device or the exercise equipment, while the user is utilizing at least one of the medical device or the exercise equipment, to determine the user information.

* * * * *